United States Patent [19]
Gayet et al.

[11] Patent Number: 6,100,396
[45] Date of Patent: Aug. 8, 2000

[54] METHOD FOR PURIFYING LACTAMS

[75] Inventors: Hubert Gayet, Villeurbanne; Philippe Leconte, Meyzieu; Philippe Perrona, Montluel, all of France

[73] Assignee: Rhodia Fiber and Resin Intermediates, Courbevoie Cedex, France

[21] Appl. No.: 09/230,588

[22] PCT Filed: Jul. 31, 1997

[86] PCT No.: PCT/FR97/01426

§ 371 Date: Apr. 23, 1999

§ 102(e) Date: Apr. 23, 1999

[87] PCT Pub. No.: WO98/05636

PCT Pub. Date: Feb. 12, 1998

[30] Foreign Application Priority Data

Aug. 2, 1996 [FR] France .................. 96 09973

[51] Int. Cl.[7] ................ C07D 201/08; C07D 201/16
[52] U.S. Cl. ................ 540/539; 540/540; 540/451; 546/243; 548/553
[58] Field of Search .................. 540/540, 539, 540/451; 546/243; 548/553

[56] References Cited

U.S. PATENT DOCUMENTS

| | | | |
|---|---|---|---|
| 2,357,484 | 9/1944 | Martin et al. | 540/539 |
| 2,405,969 | 8/1946 | Martin | 540/540 |
| 2,828,307 | 3/1958 | Soeterbroek et al. | 540/540 |
| 3,248,388 | 4/1966 | Wintersberger et al. | 540/540 |
| 5,496,941 | 3/1996 | Ritz | 540/540 |

FOREIGN PATENT DOCUMENTS

| | | |
|---|---|---|
| 0 251 852 | 7/1988 | European Pat. Off. . |
| 850 746 | 7/1949 | Germany . |
| 924 213 | 2/1955 | Germany . |

OTHER PUBLICATIONS

Chemical Abstracts, vol. 68, No. 2, Jan. 8, 1968, Columbus, Ohio, US; Abstract No. 6128, Temple, Diana M. "Liquid ion–exchange separation of some physiologically active amines", XP002027598 see abstract & Australas. J. Pharm. (1966), 47(559), S62–S64.

*Primary Examiner*—Bernard Dentz
*Attorney, Agent, or Firm*—Burns, Doane, Swecker & Mathis, L.L.P.

[57] ABSTRACT

A method for purifying lactams by liquid-liquid extraction and/or processing with an ion exchange resin is disclosed. The method is useful for purifying lactams produced by the cyclising vapour-phase hydrolysis of an aliphatic aminonitrile, and comprises removing the major part of the ammonia before subjecting the lactam to liquid-liquid extraction by means of a solvent including an acidic solvent and/or contacting said lactam with a cation exchange resin. In most applications of the lactam, it is preferable to carry out a hydrogenation step on the compounds of the lactam solution comprising unsaturations, prior to or in addition to the liquid-liquid extraction step and/or the acidic resin contact step. The purification method may also include an oxidation step in addition to or instead of the hydrogenation step. Said method is preferably combined with a distillation step in the presence of a base.

22 Claims, No Drawings

METHOD FOR PURIFYING LACTAMS

This application derives priority under 35 U.S.C. 371 from PCT/FR97/01426 filed Jul. 31, 1997.

The present invention relates to the purification of lactams by liquid-liquid extraction and/or treatment with ion-exchange resin.

Among the most common lactams, caprolactam is a very important compound, since it is a starting material for polyamide 6 which is used in considerable amounts worldwide.

One process for obtaining caprolactam, and by analogy other lactams, is to carry out a cyclizing hydrolysis of the corresponding aminonitrile, 6-aminocapronitrile, to give caprolactam.

A simple distillation of the lactam thus obtained is not sufficient to give the said lactam a purity which is compatible with the quality required for the applications of the corresponding polyamide. This is the case most particularly as regards caprolactam for the textile applications of polyamide 6.

Amounts of unconverted aminonitrile which are still too large remain, as well as smaller, but nevertheless excessive, amounts of other by-products.

The lactam and the aminonitrile from which it is derived could theoretically be separated by distillation. However, it turns out in practice that during heating, a certain amount of an addition product of these two compounds is probably formed, this addition product subsequently retrograding and re-releasing the aminonitrile which it was desired to separate. Consequently, a simple distillation does not allow excellent separation of aminonitrile and lactam.

Patent WO-A-96/20923 recommends a process for purifying caprolactam which involves the following sequence of operations. Firstly, caprolactam is prepared by reacting 6-aminocapronitrile with water, the light compounds and the heavy compounds in the crude caprolactam are then removed, after which the caprolactam obtained from the above step is treated with hydrogen in the presence of a catalyst, at a temperature of 50–150° C. and at a pressure of from 1.5 to 250 bar, to give a mixture A, which is either passed in the form of a solution in a solvent, on an ion-exchange resin containing acidic functions, or is distilled off in the presence of sulphuric acid, and finally the mixture B1 or B2 obtained in one of the above two steps is distilled in the presence of a base to give the pure caprolactam.

When that patent is analysed in greater detail, it is observed that the process is very intimately linked with the purification of the caprolactam prepared by liquid-phase hydrolysis. This emerges very clearly from the examples for carrying out the invention.

It is also observed that the purification process described is a complex process comprising multiple steps. It also appears to be very expensive and very energy-intensive, since the first step after the preparation of the caprolactam consists practically in distilling all of the products obtained from the reaction. Indeed, it is envisaged to distil the light products, i.e. the products with the lowest boiling points, and to separate out the heavy products, i.e. the products with the highest boiling points. This therefore necessarily involves the distillation of all of the caprolactam which, by definition, has a boiling point which is intermediate between those of the light products and the heavy products.

The Applicant has found, unexpectedly, relative to the teaching of patent WO-A-96/20923, that lactams prepared by cyclizing hydrolysis of aminonitriles in a vapour phase can be obtained in a purity of the same order as those of the lactams prepared in a liquid phase, by using a purification process which does not involve the prior distillation of all of the constituents of the reaction mixture obtained from the hydrolysis reaction.

The only operation prior to the present purification process is the removal of the ammonia formed, this removal usually consisting in distilling off the said ammonia.

The present invention consists of a process for purifying a lactam obtained from the cyclizing vapour-phase hydrolysis of an aliphatic aminonitrile, characterized in that, after most of the ammonia contained therein has been removed, the said lactam is subjected to a liquid-liquid extraction using a solvent comprising a solvent of acidic nature, and/or the said lactam is placed in contact with a cation-exchange resin.

The lactam used in the present process is more particularly chosen from those which are obtained by cyclizing vapour-phase hydrolysis of an aliphatic aminonitrile of general formula (I):

$$N\equiv C-R-NH_2 \quad (I)$$

in which R represents an alkylene radical containing from 3 to 12 carbon atoms.

Among lactams, the most important ones are those which serve as starting material for the preparation of polyamides 4, 5, 6 and 10 and which are obtained from aminonitriles of formula (I), in which the symbol R represents a linear alkylene radical containing 3, 4, 5 or 9 carbon atoms.

As mentioned above, caprolactam, whose polymerization gives polyamide 6, which is prepared from 6-aminocapronitrile (or ε-capronitrile) and thus contains a certain amount of the latter compound, is the preferred lactam used in the process of the invention.

As a non-limiting illustration of the process for preparing lactam by cyclizing vapour-phase hydrolysis of aminonitriles of formula (I), reference may be made, for example, to patents EP-A-0,659,741, U.S. Pat. No. 2,357,484 or WO-A-96/22974.

The lactam to be purified is preferably in the form of an aqueous solution. The lactam concentration of such a solution is generally from 20% to 80% on a weight for weight basis. The amino nitrile usually represents up to 15% of the weight of the lactam and preferably from 0.1% to 10% of this weight.

The ammonia which is formed during the cyclizing hydrolysis of the amino nitrile in a molar amount equal to that of the lactam, is still partially in the solution of the said lactam. It is generally removed by distillation.

This distillation can be carried out by heating the caprolactam solution to a foot temperature of from 100° C. to 190° C., preferably from 140° C. to 160° C., at an absolute pressure of from 1 to 10 bar, without these values being considered as critical. The choice of the operating conditions is made such that more than 50% and preferably more than 90% of the ammonia is thus removed while at the same time distilling only a relatively minor part of the water, so as not to obtain a solution with a lactam concentration of greater than 80% on a weight for weight basis.

The solvent of acidic nature used in the liquid-liquid extraction can be, in particular, a carboxylic acid or an alkyl hydrogen phosphate and more particularly a dialkyl hydrogen phosphate. Thus, it is possible to use a dialkyl hydrogen phosphate in the formula of which the linear or branched and preferably identical alkyl groups contain from 1 to 12 carbon atoms. Among these compounds, bis(2-ethylhexyl) hydrogen phosphate is most often used, in particular on account of its large-scale commercial availability. The dialkyl hydrogen phosphate can contain a certain proportion of corresponding monoalkyl hydrogen phosphate, this compound also being formed during the preparation of the dialkyl hydrogen phosphate. Generally, this proportion of monoalkyl hydrogen phosphate does not exceed 20% and is preferably less than or equal to 10% on a weight for weight basis. As carboxylic acid, mention may be made, for example, of heptanoic acid or 2-ethylhexanoic acid.

When the solvent of acidic nature is relatively viscous, it may be useful to use it for the liquid-liquid extraction mixed with another organic liquid, which will be referred to in the present text as a diluent. This diluent should dissolve only a little amount of lactam under the working conditions. The solubility of the lactam in the diluent is generally less than or equal to 200 grams per litre at 25° C. and preferably less than or equal to 100 grams per litre.

The proportion of diluent in the liquid used to carry out the liquid-liquid extraction of the process of the invention usually ranges from 0% to 80% and preferably from 10% to 60% on a weight for weight basis.

The extraction is carried out according to the known methods such as, for example, counter-current circulation of the lactam solution and of the extraction solvent, the term "extraction solvent" encompassing the solvent of acidic nature alone, as well as the mixtures thereof with a diluent.

Contactors are conventionally provided in liquid/liquid extraction, these being either stages of mixer-decanter type, or differentials of gravity column type. This second family is divided in two sub-families: non-stirred columns and mechanically stirred columns. In the first case, these are essentially packed columns or perforated-plate columns, and in the second case these are essentially pulsed or stirred columns.

The choice of the technology makes it possible to obtain the best compromise between its cost, in terms of capital and running, and its efficacy by taking into account various criteria such as the ratio of the solvent phases/product to be purified, the extraction efficacy, the floor bulk of the device, the total volume of liquid in the device, the capacity to treat solutions containing impurities in suspension and the corrosion of the materials used.

The volume ratio between the aqueous lactam solution subjected to the extraction and the extraction solvent usually ranges between 1/5 and 5/1. Preferably, this ratio is between 2/1 and 1/2.

The temperature at which the extraction is carried out can be, in particular, between 10° C. and 90° C. The process is preferably performed at a temperature of from 20° C. to 80° C.

Cation-exchange resins are polymeric resins containing functions of acidic nature. They are generally, but not exclusively resins, bearing sulphonic acid or carboxylic acid functions. Cation-exchange resins of complexing nature can also be used, which will be encompassed in the present text within the resins containing acidic functions. These cation-exchange resins of complexing nature generally contain functions of imidodiacetic or aminophosphonic type. These products, which are less commonly used and are more expensive than the other cation-exchange resins, are also more selective and more effective, on account of the combination of the ion-exchange and complexation properties.

Sulphonic resins are of two types: resins with a gel structure whose internal bead porosity is natural, resins of macroporous structure whose internal porosity is artificial and is determined by the presence of channels (pore diameter ranging up to 150 nm)

Macroporous resins are more highly crosslinked than gel-type resins. The degree of crosslinking corresponds to the weight percentage of divinylbenzene in the monomer.

In general, the increase in the degree of crosslinking entails an increase in resistance to an oxidizing medium, the rigidity of the beads, and thus the resistance to attrition and to osmotic pressures (pressure in the pores due to the change of size of the bounded ions and of their hydrated layer), the resistance to internal transfer associated with a more dense structure (lower speed of circulation of the ions in the porosity), the affinity and the selectivity of the resin for the various ionic species. On the other hand, a decrease in the total exchange capacity and in the elution efficacy are observed.

In the context of the present invention, the cation-exchange resins containing sulphonic acid functions and containing a macroporous structure are particularly suitable. The reason for this is that this structure gives the beads of resin greater solidity when the nature of the medium changes between the adsorption and the other phases of the cycle: medium of organic nature for the adsorption, aqueous medium for the washes and the elution.

The aqueous lactam solution can be placed in contact with the cation-exchange resin without addition of an intermediary solvent. If necessary, it can be diluted with water.

As a guide, the lactam solution treated with a cation-exchange resin generally comprises from 10% to 90% of dissolved compounds by weight relative to the weight of the solution, and usually from 20% to 80%.

For an industrial use, the treatments on resin are carried out very generally in a column and preferably using at least two columns working alternately.

The treatment cycle on a bed of resin is generally composed of a step of adsorption, a step of rinsing after adsorption, a step of regeneration of the bed by placing in contact with a solution of a protic inorganic acid, and a step of rinsing after elution of the regeneration flow.

The adsorption step consists in exchanging cations (protons and ammonium) between the resin and the lactam solution to be treated (feed solution). The flow of the solution in the bed can be carried out either from the top downwards (blocked-bed process) or from the bottom upwards (floating-bed process). The operation is interrupted when the saturation front reaches the end of the bed of resin.

The main aim of the rinsing step after adsorption is to avoid polluting the eluate with the feed solution contained in the bed of resin after adsorption. It is generally carried out with water and can be carried out in two successive steps. The first rinsing step consists in displacing the feed solution contained in the interstitial volume of the bed after adsorption, in order to recover it, to upgrade it. The amount of water generally required is approximately equal to the interstitial volume of the bed (or external porosity of the bed) on the assumption that the distribution of the liquid entering is correct and the bed has no preferred passage. The second rinsing step consists of the actual rinsing of the resin in order to free the pores in the resin beads of traces of the feed solution. The amount of water in this case is dependent on the nature of the resin (internal porosity) as well as on the operating conditions (in particular the flow rate of water in the bed). Overall, the transfer of material between the pores and the rinsing solution is limited by the internal diffusion kinetics in the beads.

Regeneration of the resin consists of treatment (in particular in the form of percolation) using a solution of protic inorganic acid such as, for example, sulphuric acid, nitric acid or hydrochloric acid. This solution is generally concentrated. It contains, for example, from 1 to 3 equivalents of $H^+$ per litre. This operation allows the regeneration of the active sites in the form of protons and, depending on the acid used, entails the formation of an eluate which is rich in sulphates, nitrates or chlorides of the amines retained on the resin, in particular of aminocapronitrile.

The direction of flow of the liquid in this regeneration step can be the same as that in the adsorption step (co-current regeneration) or can be in the reverse direction (counter-current regeneration). This second type of regeneration is generally more effective and is the one usually preferred. Co-current regeneration is carried out with a direction of passage of the liquid in the bed of resin which is either ascending or descending. In the first case, the bed must be blocked (for example by a slight pressure of an inert gas above the bed) in order to avoid fluidization of the resin beads. This raising of the bed would have the consequence, on the one hand, of reducing the efficacy of the elution, and, on the other hand, of mixing the various layers of the bed of resin which are more or less well regenerated. In the second case, it is not necessary to envisage blocking the bed. On the other hand, such a blockage (preferably mechanical) is necessary during the adsorption step, which then takes place from the bottom upwards. Such a mechanical blockage takes place, for example, by means of a roughcast ceiling.

The rinsing step after regeneration can be composed, as for the rinsing step after the adsorption, of two successive steps: displacement of the interstitial volume and rinsing of the beads of resin in order to remove the final traces of acid contained in the porosity of the beads. The direction of the rinsing is the same as that of the regeneration.

Although the process for purifying the lactam described above already leads to a lactam of correct purity, it is preferable, for most applications of the said lactam, and most particularly for caprolactam, to carry out or combine the liquid/liquid extraction step and/or the step of passage over acidic resin with a step of hydrogenation of the compounds in the lactam solution, which contain unsaturations. These compounds are mainly the compounds which contain nitrile functions, such as the starting aminonitrile or certain by-products containing imine functions or carbon-carbon double bonds.

The hydrogenation is preferably carried out before the passage over resin and/or the liquid/liquid extraction, these latter treatments thus making it possible to remove the amines formed by hydrogenation.

This hydrogenation step is generally carried out at a temperature of from 50° C. to 150° C., at a pressure, at the established temperature, of from 1 to 100 bar and in the presence of a hydrogenation catalyst.

Hydrogenation catalysts which may be mentioned are catalysts based on Raney nickel and/or on Raney cobalt, optionally, but preferably, containing a doping element chosen from the elements in groups IVb, VIb, VIIb and VIII of the Periodic Table of the Elements as published in the Handbook of Chemistry and Physics, 51st Edition (1970–1971).

The catalyst based on Raney nickel and/or on Raney cobalt used in the process can thus contain, besides the nickel or the cobalt and the residual amounts of the metal removed from the original alloy during the preparation of the catalyst, i.e. generally aluminium, one or more other doping elements, such as, for example, chromium, titanium, molybdenum, tungsten, iron or zinc.

Among these doping elements, chromium and/or iron and/or titanium are considered to be the most advantageous. These doping elements usually represent, by weight relative to the weight of nickel or cobalt, from 0% to 15% and preferably from 0.1% to 10%.

The catalyst can also consist of a metal, which is generally a metal from group VIII of the Periodic Table of the Elements, such as ruthenium, rhodium, iridium, osmium, platinum, palladium, nickel or cobalt, deposited on a support which is generally a metal oxide such as aluminas, silicas, aluminosilicates, titanium dioxide, zirconium oxide or magnesium oxide.

In the supported metal catalysts, the metal generally represents from 0.1 to 80% of the weight of the support and preferably from 0.5 to 50%.

The hydrogenation step can be combined or replaced with an oxidation step. Preferably, the oxidation step will be a step which replaces the hydrogenation step rather than an additional step.

The oxidation can be carried out using hydrogen peroxide, ozone or oxidizing salts such as potassium permanganate.

Preferably, the oxidation is carried out with hydrogen peroxide in basic medium, in particular in a medium containing an alkali metal hydroxide.

When the process of the invention includes an oxidation step, this can precede or follow the liquid/liquid extraction step and/or the step of passage over acidic resin, but it is preferably performed after the liquid/liquid extraction step and/or the step of passage over acidic resin.

The process according to the invention is most preferably completed by isolating the caprolactam by distillation from its aqueous solution which has undergone the various purification steps detailed above.

This distillation is carried out under the conditions usually used for caprolactam. Thus, it will preferably be carried out at a pressure below atmospheric pressure, in order to avoid subjecting the caprolactam to high temperatures over an excessive period. The absolute pressure will usually be between 100 Pa and atmospheric pressure and preferably between 100 Pa and 20 kPa. Generally, it is advantageous not to exceed a temperature of about 150° C. in the boiling vessel during the distillation. Preferably, the distillation will be carried out in the presence of a base. The base can be chosen from alkali metal hydroxides, alkaline-earth metal hydroxides, alkali metal carbonates and alkaline-earth metal carbonates. Usually, the base used will be sodium hydroxide.

The apparatus used for this distillation step is the apparatus usually used. It will be advantageous to use a distillation column which has a relatively large number of theoretical plates, preferably at least 10 theoretical plates.

The amount of base used, expressed by weight relative to the weight of caprolactam, is generally between 0.01% and 2%.

The examples which follow illustrate the invention.

EXAMPLE 1

A crude mixture obtained from a cyclizing hydrolysis reaction of 6-aminocapronitrile (ACN), pre-evaporated for 30 min at 90° C. in order to remove the ammonia contained therein, has the following composition:

ACN: 0.870% on a weight for weight basis caprolactam (CPL): 59.10% on a weight for weight basis by-products: 3.17% on a weight for weight basis water: remainder to 100% by weight.

A sample of 299 g of this mixture is placed in contact with 600 g of a mixture containing 30% by weight of bis(2-ethylhexyl) hydrogen phosphate and 70% by weight of cyclohexane at a temperature of 50° C. After leaving to equilibrate, the dispersion is decanted and a sample is taken from each of the two phases, in order to monitor the distribution of the ACN and of the CPL.

The operation is repeated with the aqueous phase obtained from the first extraction (or first extraction stage), with 366 g of the same mixture of bis(2-ethylhexyl) hydrogen phosphate and cyclohexane, but at a temperature of 34° C. (second extraction stage).

The results obtained in the two extraction stages are combined in Table 1 below.

The coefficient m corresponds to the ratio of the contents by mass of the compound considered, in the two phases at equilibrium.

TABLE 1

| | ENTRY | | | | | | EXIT | | | | | | | |
|---|---|---|---|---|---|---|---|---|---|---|---|---|---|---|
| | Water | | | Solvent | | | Water | | | Solvent | | | | |
| | Mass in g | ACN in % | CPL in % | Mass in g | ACN in % | CPL in % | Mass in g | ACN in % | CPL in % | Mass in g | ACN in % | CPL in % | mACN | mCPL |
| 1st stage | 299 | 0.87 | 59.10 | 600 | 0 | 0 | 190 | 0.30 | 49.71 | 698 | 0.34 | 10.54 | 1.13 | 0.21 |
| 2nd stage | 183 | 0.30 | 49.71 | 366 | 0 | 0 | 122 | 0.04 | 47.33 | 424 | 0.10 | 7.65 | 2.50 | 0.16 |

EXAMPLES 2 TO 5

A crude mixture obtained from a cyclizing hydrolysis reaction of 6-aminocapronitrile (ACN), pre-evaporated for 30 min at 90° C. in order to remove the ammonia contained therein, has the following composition:

ACN: 5.30% on a weight for weight basis caprolactam (CPL): 56.90% on a weight for weight basis light by-products (eluting in chromatography before the CPL): 0.14% on a weight for weight basis heavy by-products (eluting after the CPL): 0.58% on a weight for weight basis water: remainder to 100% by weight.

This feed mixture is treated with an amount of macroporous sulphonic resin (brand name Amberlite 252 H®) indicated in Table 2 below. This resin, sold in protonic form, is prewashed with water and ethanol.

Two feed mixture/wet resin volume ratios are used. This ratio is determined such that the ratio (expressed in equivalents) between the ionic charge in the solution (taking only the ACN into account) and the theoretical number of active sites in the sulphonic resin is in the region of 1 (Example 2) and of 0.3 (Example 3).

The treatment consists in placing in contact, in a stirred reactor, a determined volume of feed mixture and a fixed amount of wet resin, at 80° C. After leaving to stand, a sample of liquid is taken and a gas chromatography assay is carried out, in order to determine the partition of the species between the solution and the resin: weight/weight (w/w) contents of the solution at the end of the treatment.

The same tests are carried out with a more dilute feed mixture of the following composition:

ACN: 3.30% on a weight for weight basis caprolactam (CPL): 35.70% on a weight for weight basis light by-products (eluting before the CPL): 0.09% on a weight for weight basis heavy by-products (eluting after the CPL): 0.36% on a weight for weight basis water: remainder to 100% by weight.

Table 2 below collates the main characteristics of the various examples, as well as the results obtained.

TABLE 2

| | Examples | | | |
|---|---|---|---|---|
| | Example 2 | Example 3 | Example 4 | Example 5 |
| Solution resin ratio (in eq) | 1.31 | 0.26 | 1.23 | 0.27 |
| Volume of solution | 150.7 ml | 100.9 ml | 150.8 ml | 100.5 ml |
| Volume of resin | 30.0 ml | 100.0 ml | 20.0 ml | 60.0 ml |
| Contents in % w/w | start end | start end | start end | start end |
| Water | 36.0 45.0 | 36.0 43.8 | 59.9 64.3 | 59.9 64.2 |
| Light fractions | 0.14 0.02 | 0.14 0.02 | 0.09 0.05 | 0.09 0.02 |
| ACN | 5.30 2.40 | 5.30 0.01 | 3.30 1.55 | 3.30 0.00 |
| CPL | 56.90 52.40 | 56.90 56.90 | 35.70 34.00 | 35.70 35.70 |
| Heavy fractions | 0.58 0.39 | 0.58 0.11 | 0.36 0.22 | 0.36 0.07 |

The water content in these tests has no clear influence on the behaviour of the resin with respect to the various compounds.

With a solution/resin ratio of about 0.3, an ACN content of less than or equal to 0.01% is reached.

Binding of the CPL to the resin is negligible, or even zero, whereas the light and heavy fractions show a relatively large affinity for the resin.

EXAMPLE 6

A crude mixture (containing 60% by weight of caprolactam) obtained from a cyclizing hydrolysis reaction of 6-aminocapronitrile (ACN) is heated, at atmospheric pressure, at a temperature starting at 20° C. and rising up to 111° C. in the boiling vessel, for a few hours in order to remove the ammonia contained therein.

After this operation, the solution contains 77.6%, on a weight for weight basis, of organic products whose weight distribution is as follows: 97.42% caprolactam, 1.71% on a weight for weight basis of ACN and 0.87% on a weight for weight basis of various other by-products.

This mixture is then passed, at a flow rate of 3.1 litres/hour, over a macroporous sulphonic resin (brand name Duolite A 252 H® from the company Rohm & Haas).

The passage over resin causes decolorization of the aqueous caprolactam solution: the solution goes from an orange colour to a pale yellow colour.

About 85% of the by-products were retained on the resin.

The weight content of ACN fell to 0.0006% relative to the caprolactam, while the caprolactam purity rose to 99.8%, no account being taken of the water present.

The caprolactam solution thus treated is distilled using a packed column containing approximately 20 theoretical plates, in the presence of 0.2% of NaOH relative to the caprolactam, at a pressure gradually reduced to a final value of 650 Pa, the temperature in the boiling vessel reaching a maximum of 145° C. during the distillation. The first head fraction contains the water and most of the remaining light by-products. The following fractions have a caprolactam titre of greater than 99.996% (assay by gas chromatography).

The distilled caprolactam satisfies the specifications for the preparation of polyamide 6:

permanganate index (according to ISO standard 8660): 3.24 (specification<5)

free bases: <0.06 milliequivalent (meq)/kg of CPL (specification<0.1)

volatile bases (according to ISO standard 8661): 0.45 meg/kg (specification<0.5)

Uv absorbance at 290 nm (according to ISO standard 7059): 0.047 (specification<0.05).

EXAMPLE 7

About 8 kg of a crude mixture (containing 57% by weight of caprolactam) obtained from a cyclizing hydrolysis reaction of 6-aminocapronitrile (ACN) are heated at atmospheric pressure, at a temperature starting at 20° C. and rising up to 111° C. in the boiling vessel, for a few hours in order to remove the ammonia.

After this operation, the solution contains 67%, on a weight for weight basis, of organic products whose weight distribution is as follows: 93.09% of caprolactam, 6.19% on a weight for weight basis of ACN and 0.72% on a weight for weight basis of various other by-products.

The free bases represent 706 meq/kg, the permanganate value is 93 and the volatile bases represent 620 meq/kg.

The permanganate value is a different characteristic from the permanganate number. It corresponds to the number of millilitres of 0.2 N potassium permanganate solution consumed per kilogram of caprolactam in sulphuric medium.

A continuous hydrogenation is carried out on a portion of the caprolactam solution. 670 g of this solution are loaded into a 1.3 l stirred autoclave which allows continuous operation, along with 30 g of Raney Ni containing 1.7% of Cr and 0.8 mol of KOH/kg of Ni.

The autoclave is heated to 800° C. at a pressure of 20 bar of hydrogen, and is then fed with the caprolactam solution at a rate of 500 g/h and aqueous 1 N KOH solution at a rate of 29 g/h.

The weight distribution of organic products in the hydrogenate thus obtained is as follows: 92.89% of caprolactam, 5.8% of hexamethylenediamine, 0.01% of ACN and 1.3% of various other by-products.

The free bases represent 1446 meq/kg, the permanganate value is 54 and the volatile bases represent 116 meq/kg.

The hydrogenate is then passed over 4.4 litres of the resin defined in Example 6, under the same conditions.

The weight distribution of organic products in the solution after passage over resin is as follows: 99.92% of caprolactam, 0.08% for all of the other by-products.

The free bases represent 53 meq/kg, the permanganate value is 18 and the volatile bases represent 4 meq/kg.

The caprolactam solution thus treated is distilled continuously in three steps using a packed column containing about 45 theoretical plates, in the presence of 0.2% NaOH relative to the caprolactam, under a reduced pressure: firstly dehydration of the solution and recovery of the caprolactam at the bottom, followed by removal of the head fraction of the caprolactam and finally distillation of the caprolactam itself.

The distillation conditions are as follows: pressure of about 2000 Pa at the bottom; temperature in the boiling vessel reaching a maximum of 145° C. during the distillation.

The distilled caprolactam has a purity of 99.995% and satisfies the specifications for the preparation of polyamide 6:

permanganate index (according to ISO standard 8660): 2.9 free bases: 0.05 meq/kg volatile bases (according to ISO standard 8661): 0.18 meq/kg UV absorbance at 290 nm (according to ISO standard 7059): 0.024.

EXAMPLE 8

As in Example 7, about 10 kg of the same crude mixture containing 57% by weight of caprolactam are treated in order to remove the ammonia therefrom.

The caprolactam solution is then passed over 2 litres of the resin defined in Example 6, under the same conditions.

The weight distribution of organic products in the solution after passage over resin is as follows: 99.29% of caprolactam, 0.22% of ACN and 0.49% for all of the other by-products.

The free bases represent 258 meq/kg, the permanganate value is 95 and the volatile bases represent 48 meq/kg.

The solution obtained after passage over resin (53.1% by weight of caprolactam) is oxidized under the following conditions. 107 g of aqueous 30% sodium hydroxide solution are added and the mixture is then heated to 50° C. with stirring. 53.2 g of aqueous 30% hydrogen peroxide solution are then poured in and the mixture is maintained at 50° C. while bubbling with nitrogen for 2 hours 30.

The weight distribution of organic products in the oxidate thus obtained is as follows: 99.6% of caprolactam, 0.07% of ACN and 0.33% of various other by-products.

The free bases represent 238 meq/kg, the permanganate value is 180 and the volatile bases represent 54 meq/kg.

This oxidate is then distilled continuously with the same apparatus and under the same conditions as in Example 7.

The distilled caprolactam has a purity of 99.99% and satisfies the specifications for the preparation of polyamide 6:

permanganate index (according to iso standard 8660): 3.4 free bases: 0.07 meq/kg volatile bases (according to iso standard 8661): 0.25 meq/kg UV absorbance at 290 nm (according to ISO standard 7059): 0.032.

What is claimed is:

1. Process for purifying a lactam obtained from the cyclizing vapour-phase hydrolysis of an aliphatic aminonitrile, without prior distillation of the lactam and after most of the ammonia contained therein has been removed, said process comprising subjecting lactam to a liquid/liquid extraction using a solvent comprising a solvent of acidic nature and/or placing said lactam in contact with a cation-exchange resin, wherein the lactam used comprises those lactams obtained by cyclizing vapour-phase hydrolysis of an aliphatic aminonitrile of formula (I):

$$N\equiv C-R-NH_2 \qquad (I)$$

wherein R represents an alkylene radical containing from 3 to 12 carbon atoms.

2. Process according to claim 1, wherein the lactan used comprises those lactams obtained by cyclizing vapour-phase hydrolysis of an aliphatic aminonitrile of formula (I):

$$N \equiv C - R - NH_2 \qquad (I)$$

wherein R represents a linear alkylene radical containing 3, 4, 5 or 9 carbon atoms.

3. Process according to claim 1 wherein the lactam used is caprolactam, prepared from 6-aminocapronitrile.

4. Process according to claim 1 wherein the lactam to be purified is in the form of an aqueous solution whose lactam concentration is from 20% to 80% on a weight for weight basis.

5. Process according to claim 1, wherein the aminonitrile represents up to 15 % of the weight of the lactam.

6. Process according to claim 1, wherein the solvent of acidic nature used in the liquid/liquid extraction is an alkyl hydrogen phosphate.

7. Process according to claim 1, wherein the solvent of acidic nature used in the liquid/liquid extraction is a dialkyl hydrogen phosphate in the formula of which the linear or branched alkyl groups contain from 1 to 12 carbon atoms.

8. Process according to claim 1, wherein the solvent of acidic nature used in the liquid/liquid extraction is bis(2-ethylhexyl) hydrogen phosphate.

9. Process according to claim 1, wherein the solvent of acidic nature is used as a mixture with another organic liquid diluent, the solubility of the lactam in the diluent being less than or equal to 200 grams per litre at 25° C.

10. Process according to claim 1, wherein the proportion of diluent in the liquid used to carry out the liquid/liquid extraction in the process of the invention ranges from 0% to 80% on a weight for weight basis.

11. Process according to claim 1, wherein the volume ratio between the aqueous lactam solution subjected to the extraction and the extraction solvent ranges between 1/5 and 5/1.

12. Process according to claim 1, wherein the temperature at which the extraction is carried out is between 10° C. and 90° C.

13. Process according to claim 1, wherein the cation-exchange resin comprises polymeric resins containing functions of acidic nature.

14. Process according to claim 13, wherein the cation-exchange resin comprises cation-exchange resins containing sulphonic acid functions and containing a macroporous structure.

15. Process according to claim 13, wherein the lactam solution treated with a cation-exchange resin comprises from 10% to 90% of dissolved compounds by weight relative to the weight of the solution.

16. Process according to claim 13, wherein the treatment on resin is carried out in a column and comprises a cycle composed of an adsorption step, a step of rinsing after adsorption, a step of regeneration of the bed by placing in contact with a solution of a protic inorganic acid, and a step of rinsing after elution of the regeneration flow.

17. Process according to claim 13, wherein the regeneration of the resin is carried out using a solution of protic inorganic acid.

18. Process according to claim 1, wherein the liquid/liquid extraction step and/or the step of passage over acidic resin is preceded by or is combined with a hydrogenation step.

19. Process according to claim 18, wherein the hydrogenation step is carried out in the presence of a catalyst comprising catalysts based on Raney nickel and/or on Raney cobalt or catalysts comprising a metal from group VIII of the Periodic Table of the Elements, deposited on a support.

20. Process according to claim 1, wherein the liquid/liquid extraction step and/or the step of passage over acidic resin is preceded or followed by an oxidation step.

21. Process according to claim 20, wherein the oxidation step is after the liquid/liquid extraction step and/or the step of passage over acidic resin and is carried out using hydrogen peroxide, ozone or oxidizing salts.

22. Process according to claim 1, wherein said process is completed by isolation by distillation, in the presence of a base, of the caprolactam from its aqueous solution which has undergone various purification steps.

* * * * *